United States Patent
Baylor et al.

(10) Patent No.: US 8,019,627 B2
(45) Date of Patent: *Sep. 13, 2011

(54) MEDICAL PAYMENT SYSTEM

(75) Inventors: Dorothy M. Baylor, Rancho Santa Margarita, CA (US); Kimberly A. Darling, Trabuco Canyon, CA (US)

(73) Assignee: First Access, Inc., Mission Viejo, CA (US)

(*) Notice: Subject to any disclaimer, the term of this patent is extended or adjusted under 35 U.S.C. 154(b) by 890 days.

This patent is subject to a terminal disclaimer.

(21) Appl. No.: 12/027,196

(22) Filed: Feb. 6, 2008

(65) Prior Publication Data

US 2008/0195423 A1 Aug. 14, 2008

Related U.S. Application Data

(63) Continuation of application No. 10/338,965, filed on Jan. 8, 2003, now Pat. No. 7,346,522.

(60) Provisional application No. 60/346,705, filed on Jan. 8, 2002.

(51) Int. Cl.
*A61B 5/00* (2006.01)
*H04M 15/00* (2006.01)

(52) U.S. Cl. ............... 705/3; 705/2; 705/4; 379/114.05

(58) Field of Classification Search .................. 705/2–4; 379/114
See application file for complete search history.

(56) References Cited

U.S. PATENT DOCUMENTS

| 6,112,986 A * | 9/2000 | Berger et al. ................. 235/380 |
| 7,003,472 B2 * | 2/2006 | Sachdeva ........................... 705/2 |
| 2002/0049617 A1 * | 4/2002 | Lencki et al. ..................... 705/4 |
| 2002/0062224 A1 * | 5/2002 | Thorsen et al. ................... 705/2 |
| 2003/0076940 A1 * | 4/2003 | Manto ...................... 379/114.05 |

* cited by examiner

*Primary Examiner* — Robert W Morgan
*Assistant Examiner* — Neal R Sereboff
(74) *Attorney, Agent, or Firm* — Knobbe, Martens, Olson & Bear, LLP

(57) ABSTRACT

A medical payment system is described in which a provider of medical goods and/or services submits, via telephone or other communications medium, a request for payment amount determination for a patient encounter. A price determination system determines which of a plurality of fee schedules negotiated by the provider applies to the patient encounter and calculates, based at least in part on information entered by the provider, a payment amount for the encounter, which it communicates to at least the provider. In one embodiment, the provider receives the payment amount information while the patient is at the point of service. In one embodiment, the provider may use the system to submit a claim for payment by at least one responsible party.

20 Claims, 6 Drawing Sheets

ELIGIBILITY LIST 135

| MEMBER ID | PRIMARY MEMBER ID | EFFECTIVE DATE | TERMINATION DATE | DEDUCTIBLE BALANCE | CLAIM HISTORY | ... |
|---|---|---|---|---|---|---|
| 1234 | 1234 | 01-01-02 | – | $172 | | |
| 5678 | 1234 | 01-01-02 | – | $87 | | |
| 7920 | 7920 | 03-26-00 | 04-01-02 | – | – | |
| ⋮ | | | | | | |

*FIG. 2A*

PROVIDER LIST 140

| TAX ID | PPO AFFILIATIONS | CONTACT INFO | ZIP CODE | ... |
|---|---|---|---|---|
| 22-222-22 | PPO-2, PPO-7, PPO-22 ... | | | |
| 44-444-44 | PPO-2, PPO-3, PPO-7 ... | | | |
| ⋮ | | | | |

*FIG. 2B*

PRIORITY LIST 145

| RANK | PPO |
|---|---|
| 1 | PPO-3 |
| 2 | PPO-2 |
| 3 | PPO-7 |
| ⋮ | ⋮ |

*FIG. 2C*

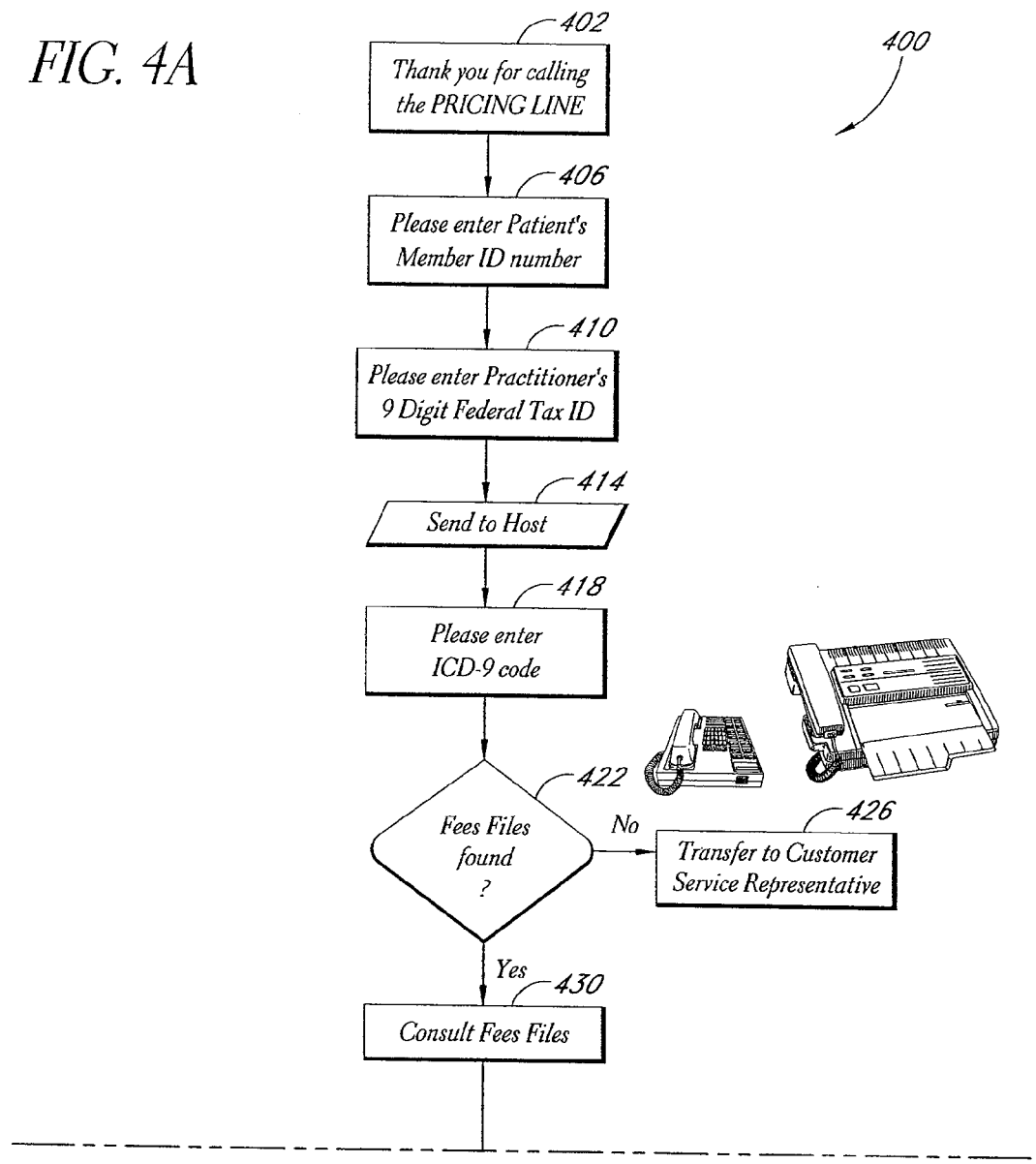

MEDICAL PAYMENT SYSTEM

PRIORITY CLAIM

This application is a continuation of U.S. patent application Ser. No. 10/338,965, filed on Jan. 8, 2003, entitled MEDICAL PAYMENT SYSTEM, and claims the benefit of priority under 35 U.S.C. §119(e) of U.S. Provisional Application No. 60/346,705, filed on Jan. 8, 2002, entitled HEALTH CLAIM SUBMISSION SYSTEM, the entirety of which is incorporated herein by reference.

BACKGROUND OF THE INVENTION

1. Field of the Invention

The present invention is related to payment systems, and, in particular, to medical payment systems.

2. Description of the Related Art

Payment amounts for medical care in the US are increasingly set by Preferred Provider Organizations (PPO's) that negotiate reduced rates with medical providers for medical services and goods provided to patients. Agreeing to accept the reduced rates offered by a PPO introduces a medical provider to the population of patients that are affiliated with the PPO. Individual medical providers may negotiate contracts with many different PPO's, each with its own negotiated fee schedule that specifies the contracted payment amount for each medical good and service offered by the provider.

Fee schedules are updated when fees change, especially when a negotiated fee is based on another rate, such as an agreed percentage off of standard Medicare rates. Fee schedule updates are typically transmitted to providers as printed pages of updates that can be kept in the provider's office in binders that may be numerous, unwieldy to handle, and difficult to reference. Attempting to quickly determine which fee schedule is the appropriate one to use for a given patient encounter can be difficult for the provider, especially when the patient belongs to a health plan with access to fee schedules from more than one PPO.

Some PPO's maintain websites that providers can access via computer network in order to get payment amount information based on the PPO's current fee schedule, but providers have thus far demonstrated reluctance to access payment information or to submit claims for payment via computer. According to one report, only 10% of providers who could use the computer to access payment amount information do so. Several factors may help to explain this fact: lack of available computer equipment at the time of patient checkout, lack of comfort on the part of the provider in using the computer and interacting with the various input requirements and interface styles of the different PPO websites, inability of the PPO website to provide a quick and easy interface to its services, and lack of speed and/or capacity of the provider's computer connection, amongst other reasons. Furthermore, having access, by paper or by computer, to individual PPO fee schedules does not help the provider determine which PPO fee schedule is appropriate to use for a given patient encounter when the patient's health plan offers access to more than one PPO fee schedule.

SUMMARY OF THE INVENTION

A medical payment system is described that allows a medical provider to communicate by telephone, using voice and/or telephone keypad, to submit information about an encounter with a patient and to receive information about an associated payment amount owed to the provider for the medical services and goods provided. In some embodiments, an interactive voice response system (IVRS) allows the provider and the price determination system to communicate in a manner that is convenient and easily understandable for the provider.

A medical payment system is described that allows a medical provider to request and to receive payment amount information for an encounter with a patient who belongs to a health plan that comprises one or more negotiated Preferred Provider Organization (PPO) fee schedules. A price determination system locates an appropriate fee schedule for the encounter and calculates a payment amount for medical goods and/or services associated with the patient encounter. For health plans that comprise a plurality of fee schedules, the price determination system accesses information about a hierarchical ranking of the fee schedules. The price determination system selects, from amongst the fee schedules negotiated by the provider, the fee schedule that has the highest ranking in the hierarchy, and uses the selected fee schedule to calculate the payment amount for the patient encounter.

In some embodiments, when payment of all or part of the calculated payment amount is the responsibility of at least one party or entity other than the patient, the provider may also use the system to submit a claim to a responsible third party or entity, such as a medical insurance company or third party administrator, a medical credit card account, or other source of funds dedicated for payment of the patient's medical expenses. In one embodiment, information about the calculated payment amount can be transmitted to a responsible third party or entity so that payment may be transmitted directly to the provider's bank account.

In one embodiment, a healthcare price determination method is described, in which the method comprises: receiving, via telephone, information about at least one patient encounter with a medical provider; determining the contracted payment amount associated with the encounter; and communicating via a voice response system the determined payment amount to at least the medical provider. The price determination method may further comprise transmitting information about the payment amount to a responsible party or entity, so that a claim for payment to the provider may be submitted, and payment may be subsequently transmitted to a bank account associated with the provider.

For purposes of summarizing embodiments of the invention, certain aspects, advantages, and novel features of the invention have been described herein. It is to be understood that not necessarily all such aspects, advantages, or novel features will be embodied in any particular embodiment of the invention.

BRIEF DESCRIPTION OF THE DRAWINGS

FIG. 2A depicts one embodiment of an eligibility list used by a price determination system.

FIG. 2B depicts one embodiment of a priority list used by a price determination system.

FIG. 2C depicts one embodiment of a provider list used by a price determination system.

FIGS. 4A and 4B (hereinafter referred to collectively as "FIG. 4") present a flowchart that depicts one embodiment of an encounter information input system.

DETAILED DESCRIPTION OF THE PREFERRED EMBODIMENTS

A medical payment system is described in which a provider of medical goods and/or services submits, via telephone or other communications medium, a request for payment amount determination for a patient encounter and in which the provider receives via an interactive voice response system (IVRS) information about the requested payment amount. A price determination system determines which of a plurality of fee schedules negotiated by the provider applies to the patient encounter and calculates, based at least in part on information entered by the provider, a payment amount for the encounter, which it communicates to at least the provider. In one embodiment, the provider receives the payment amount information while the patient is at the point of service. In one embodiment, the provider receives information about a first portion of the payment amount, if any, for which it is the patient's responsibility to pay and a second portion of the payment amount, if any, which is to be paid by another responsible party or entity. In one embodiment, the provider may use the system to submit a claim for payment to at least one responsible party or entity.

Figure 1:
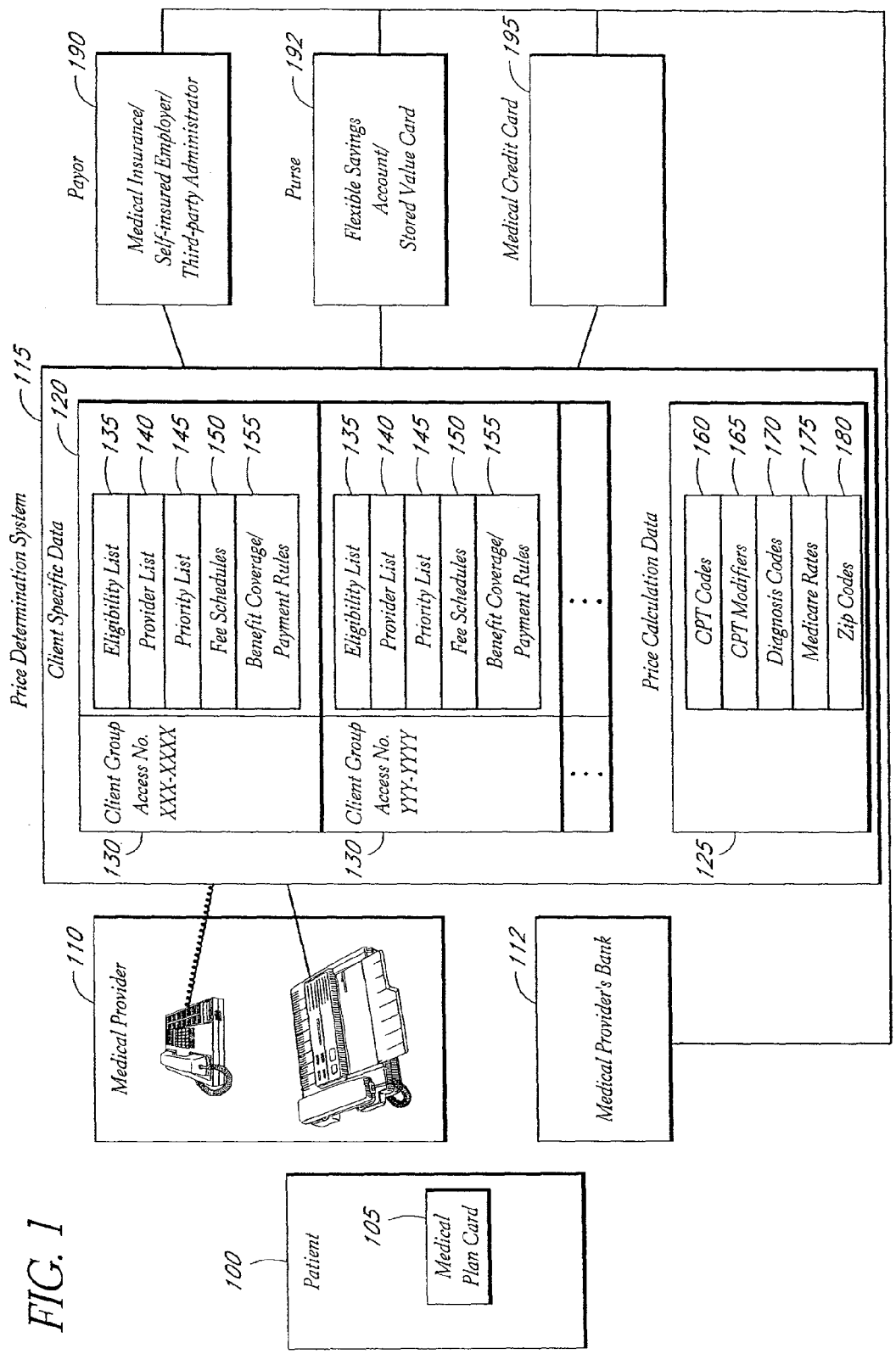
FIG. 1 depicts an overview of one embodiment of a medical payment system that comprises a price determination system.

FIG. 1 depicts an overview of one embodiment of the medical payment system. In brief, FIG. 1 depicts a system in which a patient 100 goes to a medical provider 110 for medical goods and/or services. An instance in which the patient 100 visits the provider 110 and receives medical goods and/or services can be called a patient encounter. The medical provider 110 communicates by telephone or by other communications method with a price determination system 115 in order to determine the payment amount due to the provider 110 for the encounter. The price determination system 115 calculates a payment amount, as will be described in greater detail below and communicates the amount to the provider 110 and, if applicable, to one or more parties or entities that are responsible for paying the provider 110. In one embodiment, the price determination system 115 communicates the payment amount back to the provider's office 110 immediately so that the patient 100 can pay the provider 110 before leaving the provider's office 110. In one embodiment, when some or all of the payment amount is to be paid by a third-party payor 190, such as a medical insurance company, or from a medical credit card account 195, or is to be paid from a purse 192, as will be described in greater detail below, the price determination system 115 communicates information about the payment amount to the payor 190, the purse 192 and/or the medical credit card account 195 so that payment may be made directly to a bank account 112 associated with the medical provider 110.

Describing FIG. 1 now in more detail, the provider 110 depicted may be a doctor, a pharmacist, a dentist, an optometrist, a hospital, or other medical practitioner or provider of medical goods or services. A representative of the provider 110, such as a receptionist, billing specialist, or other assistant, may initiate and execute the communication between the provider's office 110 and the price determination system 115, and, for purposes of this description, the term "provider" will refer to a provider or other person operating on behalf of the provider in communicating with the price determination system 115.

In one embodiment, the patient 100 presents to the provider 110 a medical plan card 105 that represents the patient's 100 membership in a group, known for purposes of this application as a client group, that offers a medical plan to its members. In one embodiment, access to the medical plan confers upon the patient 100 eligibility to receive medical care and/or goods at a contracted reduced rate.

The client group may provide discounted rates on medical goods and services for their members by building a medical plan from medical pricing contracts available through one or more Preferred Provider Organizations (PPO's). The PPO's negotiate pricing contracts with medical providers who agree to accept individually determined reduced payment rates for their goods and services in exchange for access to the patient base offered by the PPO. In one embodiment, the medical providers 110 also agree to accept reduced payment rates in return for a guarantee of immediate or expedited payment for patient encounters. A medical provider 110 typically contracts with a number of PPO's and may thus have agreed to accept a wide variety of contracted payment rates for each given medical good or service. For the provider 110 to determine the correct contracted rate for the goods and services associated with a given patient encounter is typically a complex and time-consuming task and often cannot be accomplished while the patient 100 is waiting to check out from the provider's office 110. Thus, the provider 110 may lose the opportunity to receive payment at the time of service and may have to expend time and money to bill the patient 100 at a later date and to hope to receive payment without enduring a protracted delay.

In one embodiment, information on the medical plan card 105 comprises a telephone number that allows the provider 110 to dial and access via telephone an interactive voice response system (IVRS) that is associated with the price determination system 115 and that is configured to accept and to transmit information about a calculated payment amount for the patient encounter, as will be described in greater detail with reference to FIGS. 3-5 below. In one embodiment, the provider 110 communicates with the price determination system 115 about a calculated payment amount for the patient encounter using a computer that is configured to access a computer network, such as the Internet, to which the price determination system 115 is also connected. In other embodiments, other methods of communication are used that allow the provider 110 to receive payment amount information for a patient encounter, including by way of example, dedicated communication lines, telephone networks, wireless data transmission systems, two-way cable systems, customized computer networks, interactive kiosk networks, automatic teller machine networks, interactive television networks, and the like.

One advantage of a telephone-based embodiment is the ease of use and uniformity of availability that it offers to the provider 110. While computers are becoming increasingly common in provider offices, discrepancies still exist in the capabilities of computer equipment and staff at provider offices. Lack of an available computer at a provider's checkout desk, lack of reliable computer network connection, slow transmission rates, and inability or unwillingness of office staff to use the computer are all conditions that currently exist. In fact, although computer systems for submitting some types of medical insurance claims for later payment do exist, statistics indicate that only around 10% of provider offices currently choose to make use of such systems. Telephones, on the other hand, are virtually ubiquitous in medical provider offices, and office staff are familiar and comfortable with their operation.

The ability on the part of the provider 110 to access payment information, whether by telephone or by other communication method, at the point and time of service represents an improvement over current systems in which the provider 110 typically waits three to six months for payment. In some current systems, the provider 110 submits a paper-based request for payment information to a PPO and must wait for a written response before being able to accurately bill the patient 100. In some current systems, the provider 110 bills the patient 100 a standard rate that may exceed the contracted PPO rate to which the patient 100 is entitled and that must later be adjusted and refunded. In such systems, even if a patient 100 desires to pay at the point of service, accurate payment amount information may not be readily available. In embodiments where a patient 100 shares responsibility for paying the provider 110 with another party or entity, such as a medical insurance company 190 or a source of funds 192 for payment of the patient's medical expenses, communicating with the price determination system 115 at the point of service allows the provider 110 to accurately inform the patient 100 of the portion of the total payment amount for which the patient 100 is responsible and to request immediate payment for that portion.

In one embodiment, communicating with the price determination system 115 also allows the provider 110 to submit a claim on behalf of the patient 100 to any parties or entities 190, 192, 195 that are responsible to pay the provider 110 for all or part of the payment amount associated with the patient encounter.

As depicted in the embodiment of FIG. 1, the price determination system 115 comprises client-specific data 120, which, when supplemented as needed by price calculation data 125, allows the price determination system 115 to accurately calculate the contracted payment amount for a patient encounter. In one embodiment, the price determination system 115 operates using computer program logic that may advantageously be implemented as one or more computer modules configured to execute on one or more processors. For the purposes of this description, computer modules may comprise, but are not limited to, any of the following: software or hardware components such as software object-oriented software components, class components and task components, processes methods, functions, attributes, procedures, subroutines, segments of program code, drivers, firmware, microcode, circuitry, data, databases, data structures, tables, arrays, or variables.

The client-specific data 120 of the price determination system 115 comprises information specific to the medical plan of the client group to which the patient 100 belongs and instructions about how payment determination is to be carried out for encounters associated with the client group. The price calculation data 125 comprises information that may apply to all or many of the client groups serviced by the price determination system 115 and that may be used for calculating a payment amount for an encounter involving a patient from any of the client groups associated with the price determination system 115. In one embodiment, client-specific data 120 is implemented as a computer module.

In one embodiment, client-specific data 120 for a given client group is indexed or accessed via a client group access number 130, and dialing the telephone number printed on the patient's 100 medical plan card 105 automatically connects the provider 110 to the appropriate client group access number 130 for the client group to which the patient 100 belongs. Thus, the price determination system 115 is able to provide payment information for patients 100 from a variety of medical plans using a single, simple, standardized interface and to quickly access the appropriate information in order to calculate an accurate payment amount for the patient encounter.

FIG. 1 depicts some examples of the types of client-specific data 120 that may be stored and used by the price determination system 115 in determining the contracted payment amount for an encounter and in submitting a claim for the determined amount to one or more responsible parties. In some embodiments, some or all of the client-specific data 120 are implemented as computer modules, as was described above.

An eligibility list 135, which will be described in greater detail with reference to FIG. 2A, comprises information about whether a given patient 100 is eligible for some, all, or none of the benefits offered to members of the client group. A provider list 140, which will be described in greater detail with reference to FIG. 2B, comprises information about providers who are affiliated with the PPO's that have contracted with the client group. A priority list 145, which will be described in greater detail with reference to FIG. 2C, comprises information about a hierarchy of PPO's that make up a medical plan and about how to determine the correct contracted rate for a provider who is affiliated with more than one PPO.

Fee schedules 150 stored with the client-specific data 120 of a given client group comprise information about how to calculate the payment amount agreed to by a given provider 110 in affiliation with a given PPO. In some embodiments, the fee schedules 150 are implemented as one or more computer modules. In some embodiments, the agreed amounts are fixed and are constant for all providers 110 affiliated with the PPO. In some embodiments, providers are grouped by their zip codes, and providers in a given zip code are paid at the same rate. In some embodiments, the payment amounts are calculated as a percentage off the provider's 110 usual billed rate for the service or good. In some embodiments, the amounts are calculated using standard Medicare rates as a basis. In some embodiments, rates for certain goods or services are calculated in one way, while rates for other goods or services are calculated in another way. In some embodiments, a PPO may have arrived at different agreements with different affiliated providers for various goods and services, and information describing these agreements is stored within the fee schedule 150 for the PPO. Thus, in some embodiments, the client-specific data 120 for a given client group may comprise a fee schedule 150 for each PPO that forms a part of the client group's medical plan.

Fee schedules are updated periodically, often every four to six weeks, in order to reflect changes in a PPO's contracted rates. Using the price determination system 115 to easily access current and accurate payment amount information at the point of service rather than attempting to locate the desired information in written format using the numerous and often unwieldy binders provided by individual PPO's is another advantage offered to the patient 100 and the provider 110 by the price determination system 115.

Client-specific data 120 for a client group also comprises benefit coverage/payment rules 155 that provide instructions to the price determination system 115 regarding how the patient encounter payment amount is to be calculated for the client group's medical plan and how claims to responsible parties and entities are to be submitted for the client group's medical plan. In one embodiment, the benefit coverage and payment rules 155 are implemented as one or more computer modules. Benefit coverage/payment rules 155 will be described in greater detail below, still with reference to this figure.

As described above, in addition to the client-specific data 120 indexed by client group access number 130, the price determination system 115 also comprises general purpose price calculation data 125 that may be useful for determining a contracted payment amount for a patient encounter associated with any client group. Some examples of such price calculation data 125 are depicted in FIG. 1.

Accurately describing the procedures associated with a patient encounter can be accomplished using Current Procedural Terminology (CPT) codes 160 and CPT modifiers 165 that are defined and maintained by the American Medical Association and that are used as an industry standard to describe over seven thousand different procedures. In one embodiment, each CPT code 160 is associated with a multiplier value that is used in conjunction with information from the fee schedule 150 to calculate the contracted payment amount. For example, a fee schedule may indicate that for providers in a given zip code area, all procedures with CPT codes 160 beginning with a "9," which indicates an office visit procedure, are paid at a rate of $5.40 per multiplier unit. If an extended office visit, with CPT code "90028," has a multiplier value of 8.2, then a provider 110 in the given area who requests pricing for an extended office visit will be given the PPO-negotiated payment amount of $44.28. In one embodiment, the price calculation data 125 also comprises Health Care Procedure Codes (HCPC), which use a five-digit alphanumeric system to identify coding categories not covered by CPT codes.

Other price calculation data 125 that may be stored by the price determination system 115 are ICD-9 codes 170, which are an industry standard used to describe medical diagnoses, current Medicare rates 175, which may be used in some situations as the basis for a PPO-negotiated payment amount, and tables of zip codes 180. Some, all, or none of these types of data, along with other data used by the price determination system 115 to calculate a contracted payment amount for a patient encounter and for apportioning responsibility for paying the payment amount may be stored as general purpose price calculation data 125. In some embodiments, some or all of the price calculation data 125 is implemented as one or more computer modules.

Using information from the client-specific data 120 and any necessary price calculation data 125, the price determination system 115 is able to calculate the appropriate contracted payment amount for the patient encounter.

As was described briefly above, the client-specific data 120 comprises benefit coverage and payment rules 155 that instruct the price determination system 115 on how to calculate the contracted payment amount and, if desired, how to further process the payment amount information for a given client group's medical plan. In some embodiments, the benefit coverage and payment rules 155 allow the price determination system to accommodate health plans in which responsibility for paying some or all of the contracted payment amount may be shared with the patient 100 by a third-party payor 190, a medical credit card account 195, or a medical payment fund 192. The benefit coverage and payment rules 155 are formulated to suit the needs of the given medical plan and to allow the price determination system 115 to flexibly serve the needs of a wide variety of medical plans.

As an example, in one embodiment, a client group's medical plan may provide access to PPO-negotiated rates for medical goods and services that the patient 100 agrees to pay to the provider 110 in full at the point of service. In this example, the benefit coverage and payment rules 155 may instruct the price determination system 115 to use the client-specific data 120 and the price calculation data 125 to calculate the contracted payment amount and to communicate the amount back to the provider 110 verbally using the IVRS. In some embodiments, options may also be provided to send a written copy of the price determination to the provider 110 via fax transmission and/or to the patient's home address via postal service.

As another example, a client group's medical plan may provide access to PPO-negotiated rates for medical goods and services that the patient 100 agrees to pay to the provider 110 in full at the point of service using a dedicated medical credit card 195. In one embodiment, a medical credit card 195 is different from a regular credit card in that charges made to the medical credit card 195 will only be approved if the credit card company receives, prior to the request for approval, verification from the price determination system 115 that the charge is for a bona fide medical expense. In one such embodiment, the medical plan card 105 may also be the medical credit card.

In one example of a medical credit card health plan, the benefit coverage and payment rules 155 may instruct the price determination system 115 to calculate the payment amount for the encounter, to send payment amount information to the provider office 110 so that the patient 100 can pay the provider 110 using the medical plan/credit card 105 in the provider's office. The price determination system 115 further sends verification of the encounter and the payment amount to the medical credit card company 195 so that the medical credit card charge will be approved. In such an embodiment, the price determination system 115 may send a verification message to the medical credit card company 195 that comprises patient 100 identification information, provider 110 identification information, and the calculated payment amount. When the associated charge request is received by the medical credit card company 195, if the patient identification 100, the provider identification 110, and the payment amount match those received in the verification message, the charge is approved, and payment is sent to the provider's bank account 112.

In another example of a medical credit card health plan, in one embodiment the benefit coverage and payment rules 155 may instruct the price determination system 115 to calculate the payment amount for the encounter and then to transmit a charge request directly to the medical credit card company 195. Once approval of the charge is received by the price determination system 115 from the medical credit card company 195, the price determination system 115 can transmit this information back to the provider's office 110.

As another example, a client group's medical plan may provide access to PPO-negotiated rates for medical goods and services in conjunction with a "purse" 192, which, for purposes of this description, is a fund of money that is available for payment of a patient's approved medical expenses. In one embodiment, a purse 192 may be funded by the patient 100 and/or by the patient's employer. In one embodiment, funds for the purse are deducted on a pre-tax basis from a patient's 100 paycheck and are available for paying Internal Revenue Service (IRS)-approved medical expenses. Some examples of purses 192 and the names by which they are known are: flexible savings account (FSA), medical savings account, health savings account, and personal care account. In one embodiment, a medical plan card 105 used in conjunction with such a medical plan may also serve as a "stored value card."

In conjunction with this type of health plan, in one embodiment, the client-specific data 120 may further comprise a list of approved medical goods and services, which may be identified by CPT code. The eligibility list 135 may further comprise information about an available balance of funds in the patient's purse 192. The benefit coverage and payment rules 155 may instruct the price determination system 115 to consult the list of approved medical goods and services to verify that the encounter is associated with approved goods and services or to calculate an approved portion of the payment amount, if not all of the encounter's goods and services are approved. The benefit coverage and payment rules 155 may further instruct the price determination system 115 to verify that sufficient funds exist in the purse 192 to cover the approved portion of the calculated payment amount, and, in one embodiment, to submit a claim to the purse 192 so that funds covering the approved portion of the payment amount are deducted from the purse 192 and are deposited in the medical provider's bank account 112. In one embodiment, the price determination system 115 can then communicate with the provider's office 110 via IVRS and/or fax transmission information about the calculated payment amount and about any approved amount paid from the patient's FSA, or other purse.

In addition to the immediate payment advantage thus afforded to the provider 110, such a medical payment system also provides an advantage to the patient 100 in that the patient 100 need not first pay out of pocket for approved expenses and then later submit a written request for reimbursement, but may have the funds deducted from the purse 192 automatically.

In another example, the price determination system 115 may calculate the contracted payment amount on behalf of a third party payor 190 that may be responsible for paying some, all, or none of the payment amount to the provider 110. A third party payor 190 may be a medical insurance company, a self-insured employer that provides its own insurance for its employees, a third-party administrator for a self-insured employer, or another entity that is responsible for paying some or all of a patient's medical expenses and that has negotiated for discounted rates available from a set of PPO's. Thus, in some embodiments, in order to correctly determine and to apportion responsibility for paying the calculated payment amount to the provider 110, the benefit coverage/payment rules 155 may describe which medical goods and services are covered by the payor 190, as well as benefit payment levels for those that are covered.

For example, some medical plans cover well-baby check-ups, while other medical plans do not. Some plans will pay for 80% of the contracted payment amount for a basic procedure, but only 50% of certain laboratory tests. Some services, such as chiropractic treatments, may be covered for only up to ten visits a year or ten visits per injury. Some plans have an annual maximum that they will pay. Using the benefit coverage/payment rules 155, client-specific information stored about the patient in the eligibility list 135, and the calculated payment amount, the price determination system 115 is able to apportion responsibility for paying the provider 110 for the patient encounter.

The benefit coverage/payment rules 155 may instruct the price determination system 115 to submit a claim for approved expenses to the third-party payor 190. In some embodiments, such a claim comprises information desired by the payor, such as, for example, patient 110 and provider 110 identification, and CPT 160 and ICD-9 170 codes associated with the encounter, and calculated payment amount. In some embodiments, the benefit coverage/payment rules 155 will also instruct the price determination system 115 to notify the provider 110 of the claim submission and of any payment amount not included in the claim submission that remains for the patient 100 to pay.

In other examples, client groups may provide a medical plan that is a combination of the medical plans described above. For example, a health plan may offer medical insurance coverage 190 in conjunction with an FSA purse 192 that can be used to pay for approved expenses that are not covered by the medical insurance 190. Or, a health plan may offer medical insurance coverage 190 in conjunction with an FSA purse 192, as above, with the added feature of a medical credit card 195 that can be used to pay for expenses that are not covered by either the medical insurance 190 or the FSA purse 192. The flexible nature of the price determination system 115 together with the expressive capabilities of the benefit coverage and payment rules 155 allows the price determination system 115 to serve a wide variety of client groups, each with different memberships, providers, PPO affiliations, and health plans, while providing a universally-available, easy-to-use interface to the provider 110. In embodiments that access the price determination system 115 via the telephone, accessing the correct information for a given encounter may be achieved quickly and easily by dialing the provided telephone number.

FIG. 1 depicts examples of three types of parties or entities that may hold full or partial responsibility for payment of a payment amount calculated by the price determination system 115. However, as will be familiar to one of ordinary skill in the art, other types and examples of parties and entities desiring information about the calculated payment amount and payment responsibility apportionment determined by the price determination system 115 may also be incorporated in the system and are also envisioned in embodiments of the system described.

FIG. 1 depicts the client-specific data 120 and the price calculation data 125 that is used by the price determination system 115 as being stored within the price determination system 115. However, as will be familiar to one of ordinary skill in the art, in other embodiments, some or all of the information may be stored in one or more of the parties or entities 190, 192, 195 or in another external data storage facility. Accessing some or all of the client-specific data 120 and/or the price calculation data 125 externally may be accomplished using any of a variety of known communications methods, such as, for example, dedicated high-speed and/or high-volume communication lines, telephone networks, wireless data transmission systems, two-way cable systems, customized computer networks, or other data transmission methods. In such embodiments, client-specific rules instruct the price determination system 115 how and where to access the information desired for calculating the contracted payment amount and, if applicable, for processing the payment amount information in accordance with the benefit coverage and payment rules 155 of the client group.

FIG. 2A depicts one embodiment of an eligibility list 135 that may be used by the price determination system 115 to access information about the patient's 100 eligibility to receive medical goods and services at the client group's contracted reduced rates. In some embodiments, possession of the card 205 confers eligibility to participate in the medical plan. In some embodiments, client group members pay monthly for access to the benefits of the health plan, and eligibility is determined on a monthly basis. In other embodiments, eligibility is determined based upon other bases, such as, for example, upon continued employment by a given employer. In some embodiments, membership in the client group and eligibility for the contracted reduced rates of the medical plan is demonstrated in ways other than by use of the card 105.

As depicted in FIG. 2A, the eligibility list 135 comprises information that identifies the patient 100, such as, for example, a member identification number 205 assigned by the health plan. In some embodiments, a member's name is used to identify the member. In some embodiments, membership in the client group may be extended to an eligible patient's 100 family members, and in such embodiments the eligibility list 135 may comprise identifying information about the member who is considered the primary member 210. Information about an effective start date of eligibility 215 to receive the client group's contracted reduced rates and a termination date of eligibility 220, if any exists, may also be stored in the eligibility list 135 and may be used by the price determination system 115 for verifying eligibility and for calculating the contracted payment amount for the patient encounter.

In embodiments where one or more parties or entities other than the patient 100 in the provider's office 110 is responsible for paying at least a portion of the payment amount, the price determination system 115 may also use information in the eligibility list 135 to correctly apportion responsibility for the payment. In such embodiments, the eligibility list 135 may also comprise additional information, such as, for example, a balance amount remaining towards a medical plan's required deductible amount 225 and a history 230 of medical claims or other information useful for calculating and apportioning responsibility for a contracted payment amount. Information in the eligibility list 135 may be updated as best suits the needs of the client group, and in various embodiments, the eligibility list 135 is updated daily, weekly, or monthly.

FIG. 2B depicts one embodiment of a provider list 140 that may be used by the price determination system 115 to determine with which PPO's the provider 110 is affiliated and to verify that the provider 110 is affiliated with at least one of the PPO's that comprise the medical plan for the client group. The provider list 140 may also be used to identify a bank account 112 associated with the provider 110 into which funds as payment for contracted payment amounts may be deposited. The provider list may also store and provide other provider-related information as desired by the individual client groups.

As depicted in FIG. 2B, the provider list 140 comprises identifying information 235, which in FIG. 2B is embodied as the providers' tax identification numbers. Identification information can also be embodied in different forms, and in some embodiments, the provider list 140 stores identification for the provider 110 as well as for a group, such as a hospital or doctor's group, to which the provider 110 belongs. Bank account information 241 allows for direct deposit of payment amounts in the provider's bank account 112, and zip code information 242 allows for accurate calculation of the payment amount when it is based, all or in part, on the provider's geographic location. The provider list 140 also comprises a list of the PPO affiliations 240 for each provider 110, which is used by the price determination system 115, in conjunction with the priority list 145 that will be described with reference to FIG. 2C, to identify an appropriate PPO whose fee schedule 150 will be used to calculate the contracted payment amount, as will be described in greater detail below with respect to FIGS. 3 and 5.

As was described above, a medical plan may comprise fee schedules 150 that have been negotiated with providers 110 by a plurality of PPO's. As was also described above, a provider 110 is often affiliated with a plurality of PPO's and may have contracted with different PPO's to provide goods and services at varying rates. In one embodiment, in order to know which contracted payment rate applies to goods or services offered by a provider 110 to a patient in a given client group, the client group builds its medical plan as a hierarchy of PPO fee schedules 150 that is encoded in the priority list 145. Thus, a PPO in the health plan is assigned a ranking, and providers 110 who serve patients 100 in the client group agree to accept the fee schedule negotiated with the health plan's top-ranking PPO, if the provider 110 is affiliated with the top-ranking PPO, and otherwise with the highest-ranking PPO with which the provider 110 is affiliated.

FIG. 2C depicts one embodiment of a priority list 145 that is used by the price determination system 115 to determine which fee schedule 150 to use for calculating the contracted payment amount. As depicted in the example in FIG. 2C, the priority list 145 comprises the list of PPO's 250 whose fee schedules are used by the health plan, as well as a ranking 245 for each PPO. Using the priority list 145, along with any applicable rules from the client-specific benefit coverage and payment rules 155, allows the price determination system 115 to know what fee schedule 150 to use to calculate a payment amount when the provider 110 is affiliated with more than one PPO, as is often the case.

In some embodiments, the PPO affiliations 240 associated with a given provider identification 235 are organized in an ordered format. For example, in embodiments where the PPO's in the PPO affiliation list 240 are listed by business name, the PPO's may be listed alphabetically by business name. In embodiments where the PPO's in the list 240 are given an identification number, the PPO's in the list can be listed, for example, in ascending or descending numerical order. In the embodiment shown in FIG. 2B, the PPO's are identified by alphanumeric code names (for example, PPO-1, PPO-2), and the lists of PPO affiliations 240 are ordered in ascending order of the numeric portion of the code names. Thus, the PPO affiliation list 240 for the provider 110 with tax identification number "22-222-22" begins with PPO-2, PPO-7, and PPO-22. The PPO affiliation list 240 for the provider 110 with tax identification number "44-444-44" begins with PPO-2, PPO-3, and PPO-7. In other embodiments, the PPO affiliations list 240 may be stored in an unordered format. The PPO affiliations list 240 for provider "22-222-22" is compared with the ranked list of PPO's 250 in the priority list 145 to ascertain the highest ranking PPO amongst the affiliates of provider "22-222-22." In the priority list 145 of FIG. 2C, the top ranking PPO is PPO-3, follow next by PPO-2 in second place, and PPO-7 in third place.

For example, to continue with our example of provider "22-222-22" from FIGS. 2B and 2C, in one embodiment, the PPO affiliations 240 from the provider list 140 are searched first for the presence of the top-ranking PPO. In this example, the top ranking PPO in the priority list is PPO-3, and the PPO affiliations list 240 for provider "22-222-22" can be searched for the presence of a listing for PPO-3.

If the PPO affiliations list 240 is ordered, as it is in FIG. 2B, a computer-implemented search beginning at the start of the list 240 can attempt to find PPO-3 in the list 240 and can determine, once the listing for PPO-7 has been reached without encountering a listing for PPO-3, that PPO-3 does not exist in the list 240. Therefore, the search for PPO-3, the highest ranking PPO in the priority list 145, among the PPO affiliations 240 of provider "22-222-22" need not be continued.

If the PPO affiliations list 240 is unordered, then a computer-implemented search can be made of the entire list 240, to see if PPO-3 is present in the list.

If a search determines that the highest-ranking PPO is not present amongst the affiliations 240 of provider "22-222-22," then a new search can be initiated, this time for the second-ranking PPO from the priority list. In the examples of FIG. 2C, the second-ranking PPO is PPO-2, and a search of the PPO affiliations list 240 for provider "22-222-22" reveals that PPO-2 is amongst the PPO's listed for provider "22-222-22."

Thus, PPO-2 is the highest-ranking PPO affiliation for provider "22-222-22," and the fee schedule 150 associated with PPO-2 will be used to determine the negotiated payment amount for the encounter.

Continuing with the example embodiments of FIGS. 2B and 2C, if the provider 110 with tax identification number "44-444-44" submits a price determination request to the same health plan for an identical encounter, the PPO-2 fee schedule 150 is not used, although provider "44-444-44" is also affiliated with PPO-2. The fee schedule 150 for PPO-3 is used, because when the PPO affiliations for provider "44-444-44" are searched for PPO-3, the highest-ranking PPO in the priority list 145, the search reveals that provider "44-444-44" is affiliated with PPO-3. Thus, PPO-3 is the highest-ranking PPO in the health plan with which provider "44-444-44" is affiliated, and the fee schedule for PPO-3 is used to determine the negotiated payment amount for the encounter.

Each client group's health plan may comprise a different set of PPO fee schedules and may order them in a different hierarchy. Thus, provider "22-222-22" and provider "44-444-44" may submit price determination requests for the same encounters as in the first example above to another client group's health plan, and may have their negotiated payment amounts calculated according to different fee schedules than those that were used in the first example. For example, if a health plan's priority list 145 comprises PPO-7, PPO-22, and PPO-45 as the three top-ranked PPO's, then a search of the affiliated PPO lists 240 for provider "22-222-22" and for provider "44-444-44" reveals that they both are affiliated with PPO-7, and they will thus both have their payment amounts calculated using the fee schedule 150 of PPO-7.

In another embodiment of a priority list 145, the list 145 for a given health plan may provide a ranking that is geographically based. For example, the priority list 145 may specify, for providers 110 in a geographical area defined by a grouping of postal zip codes, that a certain ranking of PPO's be used for selecting a fee schedule 150, while for providers 110 in another geographical area, defined by a different grouping of postal zip codes, another ranking of the PPO's be used to select the fee schedule 150. This type of geographically-based priority list 145 can reflect the fact that many PPO's are also geographically based, which is to say that they represent a network of providers within a limited geographical area, rather than being a national network with providers spread across the country. Using this type of embodiment, a health plan can, for example, structure its priority list 145 to always give highest ranking to locally based PPO's. When a provider 110 requests a price determination, the priority list 145 is consulted using the provider's 110 zip code in order to access the health plan's ranking of PPO's for that zip code. Thus, the highest-ranking PPO amongst the provider's 110 PPO affiliations 240 can be ascertained, and the appropriate fee schedule 150 for the price calculation can be located.

In another embodiment, in locations where such a health plan structure is permissible by law, a health plan may structure its priority list 145 to select the PPO fee schedule 150 that reflects the lowest cost to the patient or other payor. In such an embodiment, the priority list 145 may be organized by CPT code, such that for a given CPT code, or grouping of CPT codes, a ranked priority list 145 of PPO's is provided to reflect the PPO's that have negotiated the lowest payment amount for the given services or goods. With this type of embodiment, when a provider 110 requests a price determination, the priority list 145 is consulted using the CPT code identified by the provider 110 as describing the patient encounter for which pricing is requested. Thus, the health plan's cost-based ranking of PPO's for the given service or goods can be used to determine the appropriate fee schedule 150 to use for the payment amount calculation.

Three embodiments of PPO hierarchies and their associated priority lists have been described as examples. Other hierarchy systems are possible and priority lists 145 to suit the hierarchy systems can be created, as will be appreciated by one of ordinary skill in the art.

FIGS. 2A, 2B, and 2C depict examples of data structures that can be used to store data for the price determination system 115. However, the data used by the price determination system 115 may also be stored as other types of flat files, as relational or object-oriented data structures, or as other appropriate structures. As will be familiar to one of ordinary skill in the art, the structure, organization, and content of the data may be embodied in different forms to serve the various embodiments of the medical payment system, without departing from the spirit of the medical payment system described herein. In some embodiments, some or all of the eligibility list 135, the provider list 140, and the priority list 145 are implemented as computer modules.

Figure 3:
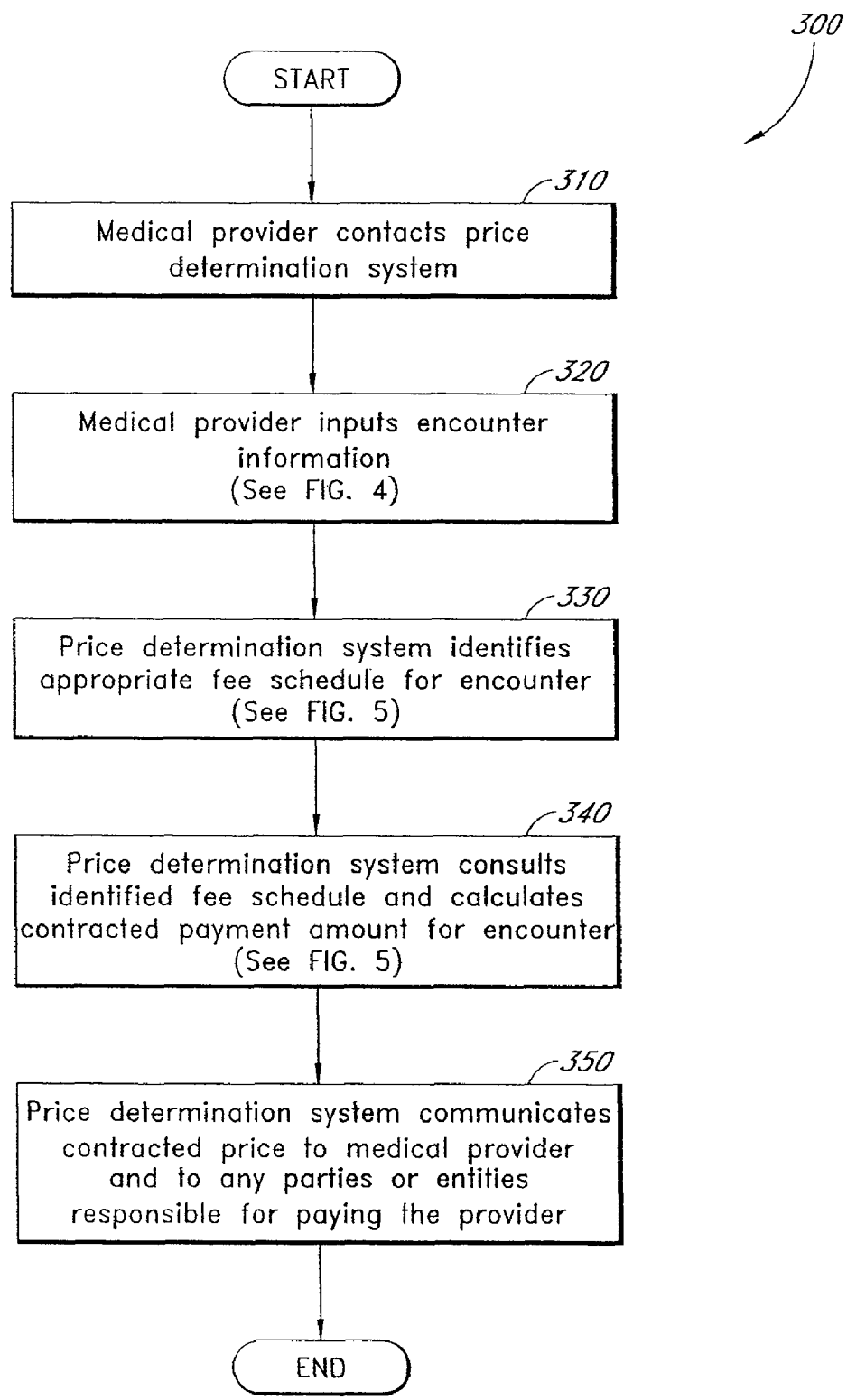
FIG. 3 is a flowchart that depicts one embodiment of a medical payment system.

FIG. 3 is a flowchart that depicts one embodiment of a medical payment system 300 that allows a medical provider 110 to contact a price determination system 115 and to receive from the price determination system 115 the correct negotiated payment amount for a patient encounter. From a start state, the medical payment system 300 proceeds to state 310, in which the medical provider 110 contacts the price determination system 115. In one embodiment, the provider 110 contacts the price determination system 115 by dialing a phone number printed on the patient's 100 medical plan card 105 and by thereby being connected to an interactive voice response system (IVRS) associated with the price determination system 115. In one embodiment, the telephone number is not printed on the medical plan card 105, and the provider 110 has access to the number for connecting to the IVRS from another source. In one embodiment, the provider 110 contacts the price determination system 115 by dialing a phone number printed on the patient's 100 medical plan card 105 and speaking to an operator. In one embodiment, the provider 110 contacts the price determination system 115 using a computer network. In other embodiments, other methods of communication, such as dedicated phone lines or wireless communications systems, are used by the provider 110 to contact the price determination system 115.

Moving on to state 320, once the medical provider 110 has contacted the price determination system 115, the medical provider 110 inputs information about the patient encounter for which the provider 110 wishes to receive a contracted payment amount. In one embodiment where the provider 110 has contacted the price determination system's 115 IVRS via telephone, the provider 110 is prompted by oral instructions transmitted from the IVRS to input the patient encounter information using the keypad on the telephone. In one embodiment, the IVRS prompts the provider 110 to input the patient encounter information orally, and the price determination system 115 uses a voice recognition system to encode the information into a format usable by the price determination system 115. In other embodiments, the provider 110 inputs the patient encounter information using a computer keyboard or other computer input system. FIG. 4 describes in greater detail one embodiment of an encounter information input system.

Moving on to state 330, once the medical provider 110 has input the patient encounter information, the price determination system 115 identifies the appropriate fee schedule for the encounter. In state 340, the price determination system 115 uses information from the identified fee schedule to calculate the contracted payment amount for the encounter. The actions of states 330 and 340 are described in greater detail with reference to FIG. 5 below.

Moving on to state 350, once the price determination system 115 has calculated the contracted payment amount for the encounter, the price determination system 115 communicates the payment amount to the provider 110 and to any parties or entities responsible for paying the provider, as indicated by the benefit coverage and payment rules 155 that were described with reference to FIG. 1. In one embodiment, where the provider 110 communicates with the price determination system 115 using an IVRS, the price determination system 115 transmits an oral message over the telephone, informing the provider 110 of the payment amount. In one embodiment, the price determination system 115 may also offer an option of having a record of the calculated payment amount faxed to the provider's office 110 so that the provider 110 can have a paper copy of the information exchanged and the calculated payment amount.

Communicating the calculated payment amount to the provider's office 110 at the time of service allows the provider 110 to present an accurate bill for the encounter to the patient 100 at the time of service, thereby enabling the patient 100 to pay the provider 110 before leaving the office. This capability represents a great improvement over current medical payment systems in which the provider 110 may typically wait three to six months to receive payment for an encounter. In one embodiment, as a condition of receiving the medical plan card 205 and access to the reduced rates that it represents, the patient 100 agrees to pay his or her portion of the calculated payment amount, in full or as otherwise agreed upon with the provider 110, at the time of service.

When one or more parties or entities, such as, for example, a third party payor 190, a purse 192, or a medical credit card account 195, is responsible for paying all or part of a calculated payment amount, the price determination system 115 may be instructed by the benefit coverage and payment rules 155 to submit a claim or a notification to the one or more responsible parties or entities. Communication with the responsible parties or entities 190, 192, 195 may take place via a dedicated high-speed, high-volume data line, via telephone connection, via computer network connection, or via another communications method. Instructions regarding the content of the claim or notification communication may be provided to the price determination system 115 by the benefit coverage and payment rules 155, so that the price determination system 115 is able to accommodate a variety of types of responsible parties and entities 190, 192, 195. When instructed by the benefit coverage and payment rules 155, the price determination system 115 can wait for feedback, such as a confirmation, from the responsible parties or entities 190, 192, 195 and can transmit an appropriate message to the provider's office 110 using the IVRS, the fax, or other chosen communications method. Such an appropriate message may, in some embodiments, be a simple confirmation of the actions taken by the price determination system 115, and may, in some embodiments, provide information about a portion of the payment amount still remaining for the patient 100 to pay.

Other embodiments can allow the price determination system 115 to process the calculated payment amount in different ways. In one embodiment, claims for submission to responsible parties 190, 192, 195 for payment are batched and are sent to the responsible parties once a day, or as is otherwise deemed desirable. In one embodiment, information is stored in a table with the client-specific data 120 that describes a price determination request for a given encounter and information about the amount of savings received by the patient 100 over the provider's standard billing rate for the encounter. Such information may be provided to the client group or to another interested, authorized party for assessing the value of the medical plan to its members.

The flowchart of FIG. 3 has depicted one embodiment of a medical payment system. As will be clear to one of ordinary sill in the art, other embodiments of the medical payment system may be implemented that arrange the states of the system in other configurations, that add or delete states as appropriate, that divide the system into different states, or that exhibit a combination of these changes without departing in spirit from the medical payment system described herein.

Figure 4B:
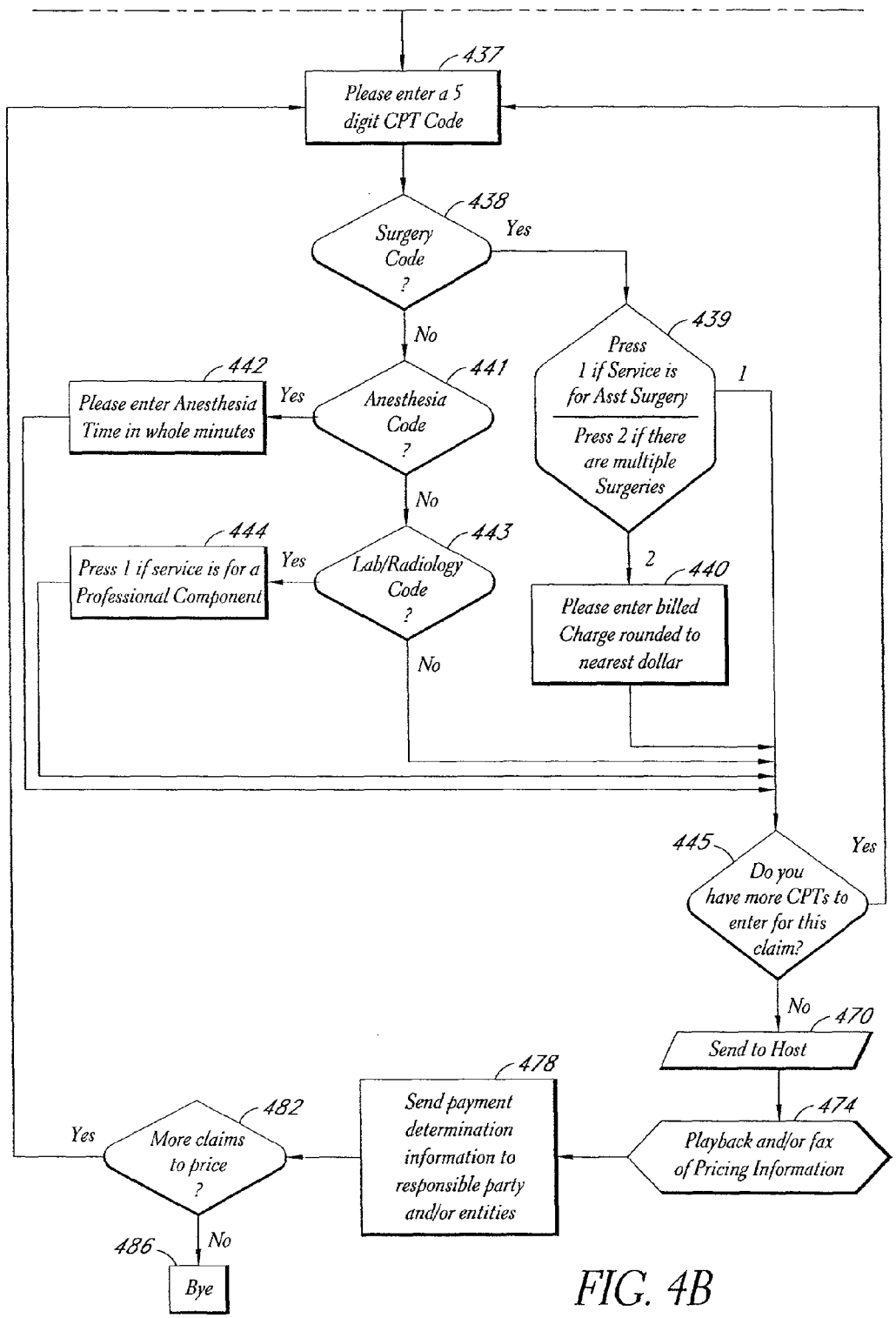

FIG. 4 presents a flowchart that depicts one embodiment of an interactive voice response system (IVRS) 400 that can be used by a price determination system 115 to receive encounter information from a provider 110 and to transmit an associated calculated payment amount back to the provider 110 and, if appropriate, to other associated parties and/or entities 190, 192, 195.

In one embodiment, communication from the provider 110 to the IVRS 400 is carried out using a touch-tone telephone keypad, and communication from the IVRS 400 to the provider 110 is carried out by recorded voice messages. Allowing the provider 110 to use the telephone keypad to enter the encounter information, which, in one embodiment, is encoded numerically, provides an accurate, quick, and easy-to-use method for inputting the encounter information. Using the keypad to enter encounter information draws upon knowledge that is common to workers in a medical provider's office 110 and does not require computer literacy or computer equipment on the part of the provider 110. Configuring the IVRS 400 to communicate verbally with the provider 110 in order to convey both instructions for use of the system and the calculated payment amount provides a familiar, easily understandable method for communicating with the provider 110. In one embodiment, additional communication from the IVRS 400 to the provider 110 may be carried out by fax transmission, especially at the end of the price determination for providing a summary in printed format of the price determination for the encounter.

In other embodiments, other methods of communication may be implemented for communications from the provider 110 to the price determination system 115, from the price determination system 115 to the provider, and from the price determination system 115 to any other relevant party or entity 190, 192, 195.

For the embodiment depicted in FIG. 4, beginning at state 402, the IVRS 400 greets the provider 110. Moving on to state 406, the IVRS 400 prompts the provider to enter the patient's 100 member identification number. In one embodiment, the patient's 100 member identification number is assigned by the client group's health plan and is printed on the patient's 100 medical plan card 105. In one embodiment, the IVRS 400 prompts the provider to enter identifying information other than a member identification number for the patient 100. Having access to identifying information for the patient 100 allows the price determination system 115 to verify the patient's 100 eligibility for the medical plan and, where applicable, allows the system 115 to access information about the patient's deductible balance remaining and prior claim history or other relevant patient-specific information.

Moving on to state 410, the IVRS 400 prompts the provider 110 to enter identifying information for the provider 110. In the embodiment shown in FIG. 4, the provider's federal tax identification number is used as a readily available and standard-formatted identifier. In other embodiments, other forms of identification may be used for identifying the provider 110. Identifying the provider 110 allows the price determination system 115 to access information about the provider's 110 PPO affiliations, the provider's bank account information 112, and the provider's contact information, geographic location, and other relevant provider-specific information.

In the embodiment shown in FIG. 4, the IVRS 400 proceeds to state 414, where the patient 100 identification information and the provider 110 identification information are sent to a host processor. In embodiments where the telephone number dialed by the provider 110 automatically connects the provider 110 to the client-specific data 120 indexed by the client group access number 130, having the patient 100 identification information allows the processor to begin accessing stored data that is used to verify patient 100 eligibility, so that the provider 110 can be notified promptly if the patient 100 is determined not to be eligible for the benefits of the client group's health plan.

Being connected to the client-specific data 120 also allows the processor to access the health plan's hierarchy of PPO's, as expressed in its priority list 145. Based on the type of PPO hierarchy used by the health plan, having the provider 110 identification information may allow the processor to begin locating the fee schedule 150 that will be used by the price determination 115 system for calculating the payment amount. For example, for health plans with PPO hierarchies similar to the example illustrated in FIG. 2C, having access to the provider 110 identification information allows the price determination system 115 to gain access to the provider's 110 list of PPO affiliations 240. Comparing this list 240 to the priority list 145 allows the price determination system 115 to identify the appropriate fee schedule 150.

In one embodiment, to identify the appropriate fee schedule 150, the price determination system 115 determines if the health plan's highest-ranking PPO is among the provider's 110 affiliates. If so, the processor locates and loads the associated fee schedule 150. If not, the price determination system 115 identifies the second-ranking PPO in the health plan's priority list 145 and once again makes a comparison with the provider's 110 PPO affiliations list 240. The price determination system 115 determines if the second-ranking PPO is the amongst the provider's affiliates. If so, the second-ranking PPO is therefore the highest ranking PPO available amongst the provider's 110 affiliations 240, and its fee schedule 150 is used for price determination. If it is not, this search process continues until the highest-ranked PPO that is both on the priority list 145 and on the provider's PPO affiliation list 120 is located.

Once the appropriate fee schedule 150 is identified, the price determination system 115 can already, "in the background," access the fee schedule 150, which will be used to calculate a payment amount for any procedure codes entered for the encounter. Fee schedules 150, which typically comprise a large volume of complex data, can sometimes be unwieldy and slow to load, and loading the fee schedule "in the background" while the provider 110 continues to communicate with the IVRS thus enhances the response speed of the system.

Other embodiments of the priority list 145 also allow for an "in the background" loading of the fee schedule.

For example, in embodiments where the PPO hierarchy is geographically-based, and where the provider list 140 comprises zip code information 242 for the provider 110, having access to the provider identification 235 allows the price determination system 115 to ascertain the provider's zip code 242 and to use that information to locate the associated PPO priority list 145. As with the previous example, having access to the priority list 145 and to the provider's 110 list of PPO affiliations 240 allows the price determination system 115 to identify the appropriate fee schedule 150.

In one embodiment in which the priority list 145 is based at least in part on the CPT codes entered by the provider 110, locating and loading the appropriate fee schedule 150 is deferred until CPT information is entered that will allow the appropriate fee schedule 150 to be located.

Moving on to state 418, in the embodiment shown in FIG. 4, the IVRS 400 prompts the provider 110 to enter information about a medical diagnosis associated with the encounter. One commonly used numeric code for communicating about medical diagnoses is called the International Classification of Diseases ($9^{th}$ Edition) code (ICD-9), and in one embodiment, the diagnosis information is entered using an ICD-9 code. In one embodiment, providing the price determination system 115 with information about the diagnosis associated with the encounter allows the system 115 to accurately determine coverage and payment levels for claims, such as medical insurance claims, that are based at least in part on diagnosis information.

Moving on to state 422, the IVRS 400 determines whether or not the host was able to locate the appropriate fee schedule 150 for the encounter. If the appropriate fee schedule 150 was not found, the IVRS 400 proceeds to state 426, where the provider 110 is transferred to a live customer service representative for completion of the price determination request. If the appropriate fee schedule 150 has been located, the IVRS 400 proceeds to state 430 where the fee schedule 150 is accessed.

Moving on to state 437, the IVRS 400 prompts the provider 110 to enter information about a medical good or service associated with the patient encounter. One commonly used numeric code for communicating about medical goods and services is the Common Procedure Terminology (CPT) code. A CPT Modifier Code for use in conjunction with the CPT code can be used to expand the expressive capabilities of the CPT codes. In one embodiment, the medical goods or services information is entered using a CPT code and, if desired, a CPT modifier code. Providing the price determination system 115 with information about the medical goods or services associated with the encounter allows the system 115 to accurately determine a contracted payment amount.

In the embodiment shown in FIG. 4, the IVRS 400 prompts the provider 110 to enter additional information in response to inputted CPT codes for procedures associated with surgery, anesthesia, laboratory work, and radiology, as is described with reference to states 438-444. CPT codes are often grouped numerically into five classes that allow for easy identification of surgery, anesthesiology, laboratory, and radiology procedures. In other embodiments, other CPT codes may receive special treatment, as suits the preferences of the client group's medical plan.

Referring first to state 438, the IVRS 400 determines if the CPT code entered by the provider 110 in state 437 is a surgery code. If the CPT code is determined to be a surgery code, the IVRS 400 proceeds to state 439, where the provider 110 is prompted to indicate if the surgery is an assisted surgery. In one embodiment, if the provider 110 indicates that the surgery was assisted, meaning that the provider 110 served as an assistant surgeon in the surgery, then the price determination system 115 is given this information. In one embodiment, the information is requested because an assistant surgeon is typically compensated at a percentage of the allowed payment amount for the primary surgeon. In state 440, the provider 110 is prompted to enter the provider's standard billed amount for the surgery, rounded to the nearest dollar, and the IVRS 400 proceeds to state 445, where the provider is prompted to indicate whether there are more CPT codes to enter in association with this encounter.

Returning to state 439, if the provider 110 responds that there are multiple surgery codes to enter, then the IVRS 400 proceeds to state 445, where the IVRS 400 cycles back to state 437 and the provider 110 is prompted to enter another CPT code. In one embodiment, the price determination system 115 has been alerted at this point that subsequent surgery codes entered are for secondary surgeries performed in conjunction with a primary surgery, because secondary surgeries are typically compensated at a lower payment amount than primary surgeries.

If, in state 438, the IVRS 400 determines that the CPT code entered in state 437 is not a surgery code, the IVRS 400 proceeds to state 441, where the IVRS 400 determines if the CPT code entered in state 437 is an anesthesia code. If the CPT code is determined to be an anesthesia code, the IVRS 400 proceeds to state 442, where the provider 110 is prompted to enter the length of time of the anesthesia procedure in whole minutes. Entering the time length for the anesthesia procedure can be accomplished easily using a telephone keypad and allows for proper calculation of the contracted payment amount for an anesthesia procedure.

If, in state 441, the IVRS 400 determines that the CPT code entered in state 437 is not an anesthesia code, the IVRS 400 proceeds to state 443, where the IVRS 400 determines if the CPT code entered in state 437 is a laboratory or radiology code. If the CPT code is determined to be a laboratory or radiology code, the IVRS 400 proceeds to state 444, where the provider 110 is prompted to indicate by means of CPT modifier code 165, whether the price determination request is for service rendered by a technician, such as a blood draw, which is considered a "technical component" and is compensated at one rate, or is for service rendered by a physician, such as analysis of blood test results, which is known as a "professional component" and is compensated at another rate.

If, in state 443, the IVRS 400 determines that the CPT code entered in state 437 is not a laboratory or radiology code, the IVRS 400 proceeds to state 445, where the IVRS 400 prompts the provider 110 to indicate whether the provider 110 has more CPT codes to enter in association with the patient encounter for which a payment amount is being requested.

If, in state 445, the provider 110 indicates that there are additional CPT codes to be entered in conjunction with the payment amount calculation request for the current patient encounter, the IVRS 400 returns to state 437 where the IVRS 400 prompts the provider 110 to enter a CPT code. The IVRS 400 continues to cycle through states 437-445 until the provider 110 indicates that there are no further CPT codes to enter in association with the current payment amount request.

When, in state 445, the provider 110 indicates that there are no further CPT codes to enter in association with the current payment amount request, the IVRS 400 proceeds to state 470, where the IVRS 400 transmits the information that was received from the provider 110 about the patient 100, the provider 110, the diagnosis (ICD-9), and the goods and services (CPT's) associated with the encounter to a host processor for the price determination system 115.

In one embodiment, the IVRS 400 proceeds to state 474 where the IVRS 400 plays a message indicating the calculated pricing information to the provider 110 over the telephone. In the embodiment shown in FIG. 4, the IVRS 400 may additionally or alternatively fax the calculated pricing information to the provider 110.

Moving on to state 478, the price determination system 115 sends the calculated payment information and any associated information indicated by the benefit coverage and payment rules 155 to any responsible parties and/or entities indicated in the benefit coverage and payment rules 155 as was described with reference to FIG. 1.

Moving on to state 482, the IVRS 400 prompts the provider 110 to indicate whether there are more claims to price for this patient. If the provider 110 indicates that there are one or more claims to price, the IVRS 400 proceeds to state 437, where the provider 110 is again prompted to enter a CPT code and to proceed as was described above. If, in state 482, the provider 110 indicates that there are no more claims to price for the patient 100, the IVRS proceeds to state 486, where the IVRS 400 indicates to the provider 400 that the interaction is completed, and the communication is terminated.

The flowchart of FIG. 4 depicts one embodiment of an encounter information input system. As will be clear to one of ordinary skill in the art, other embodiments of the encounter information input system may be implemented that arrange the states of the system in other configurations, that add or delete states as appropriate, that divide the system into different states, or that exhibit a combination of these changes without departing in spirit from the encounter information input system described herein.

Figure 5:
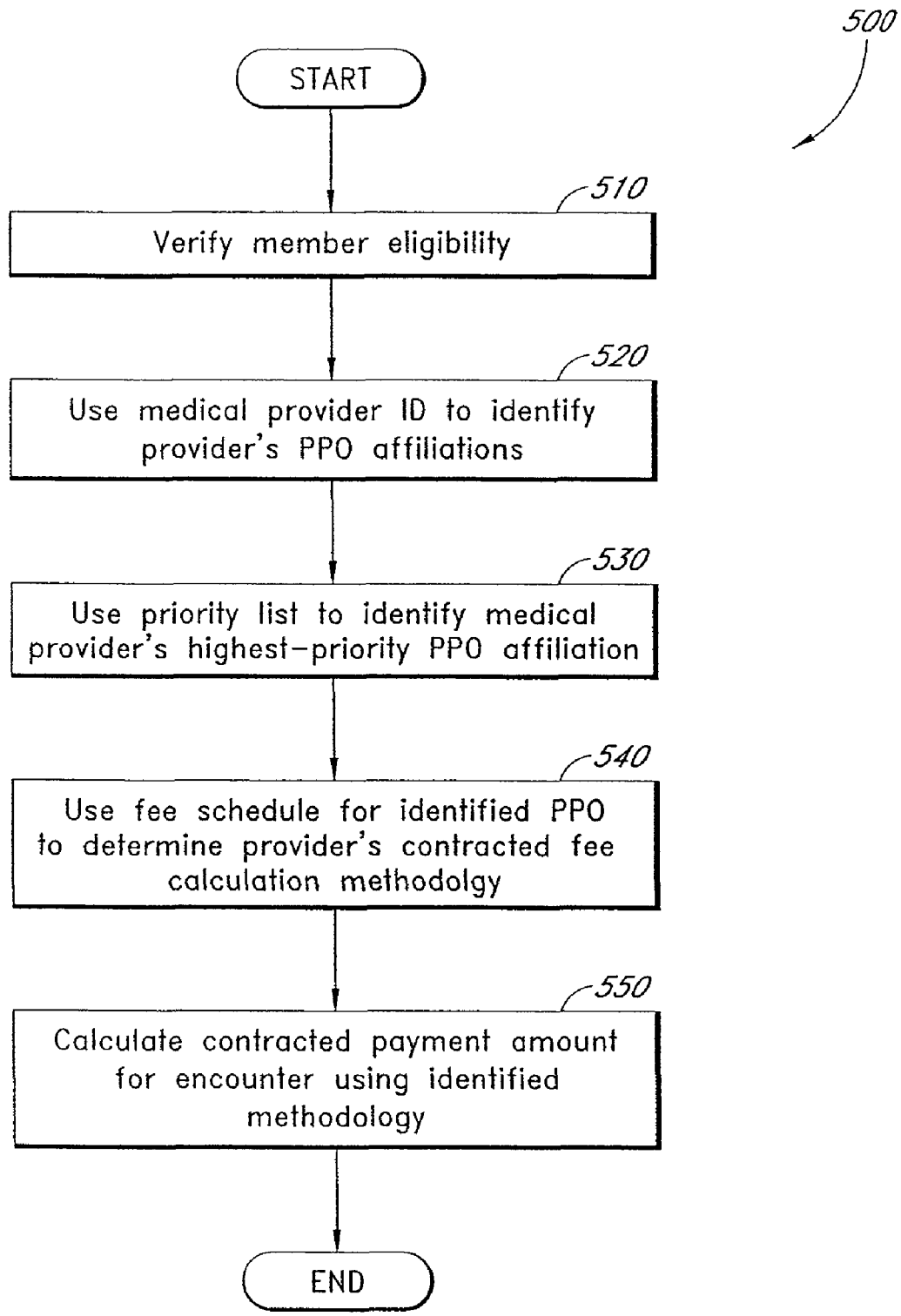
FIG. 5 is a flowchart that depicts one embodiment of a method to determine a contracted payment amount for a patient encounter.

FIG. 5 is a flowchart that depicts one embodiment of a method 500 that can be carried out by a price determination system 115 to determine a contracted payment amount for a patient encounter. The embodiment shown in FIG. 5 corresponds generally to states 330 and 340 of the medical payment system 300 described with reference to FIG. 3 above.

The method 500 of FIG. 5 begins in state 510 where the price determination system 115 verifies the eligibility of the patient 100 to receive the benefits of the medical plan associated with the client group access number 130. In one embodiment, the price determination system 115 accepts member identification information about the patient 100 from the provider 110 and uses the identification information to access eligibility information about the patient 100 stored in an eligibility list 135, as was described in greater detail with reference to FIG. 2A. For example, in embodiments in which information about the patient's effective date 215 of coverage and termination date 220 is stored in the eligibility list 135, the price determination system 115 verifies that the current date is later than the effective date 215 and that the current date is earlier than the termination date 220, if any termination date 220 is listed.

Once the price determination system 115 determines that the patient 100 is eligible to receive the benefits of the medical plan, the price determination system 115 proceeds to state 520 of the method 500, in which the price determination system 115 uses the medical provider 110 identification information entered by the provider 100 to identify the provider's 100 PPO affiliations. In one embodiment, the price determination system 115 uses the provider list 140, as was described in greater detail with reference to FIG. 2B, to identify the provider's 110 PPO affiliations.

Proceeding on to state 530 of the method 500, the price determination system 115 uses the PPO affiliation information accessed in state 520 together with information stored in the priority list 145, as was described in greater detail with reference to FIG. 2C, to identify which of the provider's 100 affiliated PPO's is given the highest priority according to the priority list 145. This information can be used to identify the fee schedule 150 that is to be used for calculating the payment amount. Basically, the PPO affiliations negotiated by the provider 110 are identified, the hierarchy of the health plan's PPO's is identified, and the two are compared in order to determine which of the PPO's affiliated with the provider 110 has the highest ranking in the health plan's hierarchy.

In various embodiments, identifying which of the provider's 110 affiliated PPO's is given the highest priority can be carried out in different ways, depending on the organization, structure, and content of the priority list 145 and of the list of PPO affiliations 240 for each provider 110. For example, whether the provider's 110 PPO affiliations are stored in an ordered or an unordered format, as well as the type of data structure used for their storage, will affect the method used for searching for and locating the given provider's 110 most highly-ranked PPO, as will be familiar to a practitioner of ordinary skill in the art. One simple example of such a search was described with reference to FIGS. 2B and 2C.

Furthermore, the type of hierarchical organization of PPO's that is used to form the client group's health plan will affect the method used in state 530 to determine which PPO's fee schedule 150 is to be used for calculating the payment amount due to the provider 110.

For example, as was described with reference to FIG. 2C, in embodiments where the health plan is organized such that for each geographical location served, a different ranking of the PPO's is used, then searching for the highest-ranking PPO may comprise identifying the zip code 242 associated with the provider 110 and identifying the portion of the priority list 145 associated with that zip code.

In other embodiments, one ranking of PPO's may be used for all geographical areas except for one area, in which, for example, a self-insuring employer has negotiated special rates with medical providers and for which another ranking exists. In such an embodiment, the benefit coverage and payment rules 155 may instruct the price determination system 115 to use the zip code 242 of the provider 110 who is submitting a price determination request to access the desired ranking of PPO's in the priority list 145.

As was also described with reference to FIG. 2C, in some embodiments where such arrangements are permissible, the health plan is organized such that the payment amount negotiated by the PPO that offers the lowest price for the services or goods associated with the patient encounter is the amount used as the contracted amount. In such embodiments, searching for and locating the appropriate fee schedule comprises identifying the CPT code or other procedure/goods identifier associated with the patient encounter and identifying the portion of the fee schedule 150 that gives a ranking of PPO's for that procedure identifier.

Procedure identifiers such as CPT codes may also be relevant to the search for an appropriate fee schedule 150 in embodiments where a given PPO does not provide a negotiated rate for the services or goods associated with the patient encounter. For example, a given PPO may not have negotiated a payment amount for eye examinations with its affiliated providers. Thus, even if the given PPO is listed in the priority list 145 as having the highest ranking in general, for patient encounters that involve an eye examination, the fee schedule associated with the PPO that has the next highest ranking and that does provide a contracted rate for eye examinations will be used. As will be familiar to a practitioner of ordinary skill in the art, the priority list 145 can be modified to express such a hierarchy.

Other embodiments may use other methods and information sources to search for an appropriate fee schedule, as encoded in the instructions of the benefit coverage and payment rules 155. For example, in one embodiment, a client group may choose to give the highest ranking to the PPO, from amongst those that make up its health plan, that contracts with the largest number of providers, and to rank the other PPO's in its health plan according to the number of providers in their network, as well. Information about the number of contracted providers participating in each PPO's network may be provided to the price determination system 115 on a daily, weekly, monthly, yearly or other basis, so that the priority list 145 in such an embodiment may be kept up-to-date.

Handling exceptions and anomalies in the selection of fee schedule 150 for use in price determination can be carried out in a variety of ways, as expressed by the benefit coverage and payment rules 155 for a given client group. In some embodiments, if a provider 110 does not appear in the client group's provider list 140, or if the identified provider 110 has no associated PPO affiliations that appear in the priority list 145, then the price determination request submitted by telephone, computer, or other communications method is forwarded to a human representative for price determination. In some embodiments, the price determination request is rejected, and a message is transmitted to the provider's office 110 that no payment amount for the encounter can be calculated using the price determination system 115.

In some embodiments, the benefit coverage and payment rules 155 for a given client group specify a default method of handling such anomalies or exceptions. In one embodiment, a default flat fee for each CPT code may be specified. In another embodiment, a fixed percentage of the provider's standard billing rate for the given service or good may be specified. In such an embodiment, the IVRS or other communications method may need to prompt the provider 110 to enter the standard billing rate for the given service or good. In other embodiments, exceptions and anomalies are handled using other methods that will be familiar to one of ordinary skill in the art.

Proceeding to state 540 of the method 500, the price determination system 115 accesses the fee schedule 150 for the PPO that was identified in state 530 as being the PPO with the highest priority from amongst the provider's 110 PPO affiliations. In one embodiment, the price determination system 115 uses the fee schedule 150 to determine the contracted calculation methodology agreed upon by the provider 110 and the provider's highest priority PPO for the medical goods and/or services with the CPT codes input by the provider 110 for the patient encounter.

Once the calculation methodology agreed upon by the provider 110 and by the PPO has been identified, the price determination system 115 proceeds to state 550 of the method 500 and uses the identified calculation methodology to calculate the contracted payment amount for the goods and services identified by the provider 100 as being associated with the patient encounter. In some embodiments, the CPT information 160 stored in the price calculation data 125 is accessed to identify the multiplier values for the entered CPT codes, as was described with reference to FIG. 1. In some embodiments, zip code information 180 and/or Medicare payment rate information 175 is accessed in order to calculate the contracted payment amount for the encounter.

Once the contracted payment amount has been calculated, the medical payment system 300 of FIG. 3 can use the payment amount information together with information stored in the client group's benefit coverage and payment rules 155 to apportion, amongst one or more parties or entities 100, 190, 192, 195, the responsibility for paying the payment amount to the provider 110. The medical payment system 300 can further communicate with the one or more parties or entities 100, 190, 192, 195 in order to notify them of the portion of the payment amount for which they are responsible to pay.

The flowchart of FIG. 5 has depicted one embodiment of a method to determine a negotiated payment amount for a patient encounter. As will be clear to one of ordinary skill in the art, other embodiments of the payment amount determination method may be implemented that arrange the states of the system in other configurations, that add or delete states as appropriate, that divide the system into different states, or that exhibit a combination of these changes without departing in spirit from the payment amount determination method described herein.

For ease of explanation, some simplifying assumptions have been made in the foregoing detailed description. For example, one-to-one correspondences have been assumed between the provider 110 and the provider bank 112, between a client group and the associated medical plan, and between a PPO and the associated priority list. Thus, for purposes of this description, for example, sending a payment to a provider's bank account 112 is equivalent to sending payment directly to the provider 110. Similarly, for purposes of this description, because the aspect of interest with respect to the client group is the medical plan that it offers its members, the terms client group and medical plan may be used interchangeably in some instances. Furthermore, the one-to-one correspondence assumed in this description for ease of explanation implies that a hierarchy or priority list of PPO's may also be seen as a hierarchy or priority list of the associated fee schedules. In other embodiments, these one-to-one correspondences may not hold true without departing from the spirit of the medical payment system described herein.

While certain embodiments of the inventions have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. A computer-implemented method of determining prices, comprising:
    prompting a provider with an interactive voice response system to enter information about a patient encounter wherein the interactive voice response system is configured to verbally prompt the provider for patient identification information, provider identification information, and goods or services information;
    receiving the patient identification information, the provider information, and the goods or services information;
    determining a payment amount associated with the goods or services wherein determining the payment amount comprises:
        selecting at least one fee schedule from multiple fee schedules based at least in part on the provider identification information; and
        calculating the payment amount based at least in part on the selected fee schedule and based at least in part on the goods or services information; and
    communicating the payment amount to at least the provider.

2. The computer-implemented method of claim 1, wherein the selecting of the one or more fee schedules is based on the zip code of the provider.

3. The computer-implemented method of claim 1, wherein the provider is at least one of the group consisting of: a doctor, a pharmacist, a dentist, an optometrist, and a hospital.

4. The computer-implemented method of claim 1, further comprising determining a portion of the payment amount to be paid by the patient and a portion of the payment amount to be paid from a source of medical funds.

5. The computer-implemented method of claim 4, wherein the source of medical funds is a third-party payor.

6. The computer-implemented method of claim 4, wherein the source of medical funds is a flexible savings account.

7. A computer-implemented method of determining prices, comprising:
    prompting a provider with an interactive voice response system to enter information about a patient encounter wherein the interactive voice response system is configured to verbally prompt the provider for patient identification information, provider identification information and goods or services information;
    receiving the patient identification information, the provider identification information and the goods or services information;
    determining at least one provider organization affiliated with the provider;
    selecting at least one fee schedule for the patient encounter based on at least the provider information;
    calculating a payment amount associated with the patient encounter based at least in part on the selected fee schedule and based at least in part on the goods or services information; and
    communicating the payment amount to at least the provider.

8. The computer-implemented method of claim 7, wherein selecting a fee schedule is based at least in part on the zip code of the provider.

9. The computer-implemented method of claim 7, wherein the provider is at least one of the group consisting of: a doctor, a pharmacist, a dentist, an optometrist, and a hospital.

10. The computer-implemented method of claim 7, wherein selecting at least one fee schedule to use comprises selecting, from amongst the plurality of fee schedules negotiated with one or more provider organizations.

11. The computer-implemented method of claim 7, further comprising determining a portion of the payment amount to be paid by the patient and a portion of the payment amount to be paid from a source of medical funds.

12. The computer-implemented method of claim 11, wherein the source of medical funds is a third-party payor.

13. The computer-implemented method of claim 11, wherein the source of medical funds is a Flexible Savings Account.

14. A computer-implemented price determination system, comprising:
    an interactive voice response system that is configured to verbally prompt a provider to enter information about a patient encounter, the information comprising patient identification information, provider identification information, and goods or services information and wherein the interactive voice response system is further configured to receive the patient identification information, the provider information and the goods or services information; and
    a computer-implemented price determination processor that is configured to calculate a payment amount associated with the patient encounter wherein the price determination processor is further configured to calculate the payment amount based at least in part on the goods or services information and by electronically accessing at least one fee schedule from multiple fee schedules based at least in part on the provider information.

15. The computer-implemented method of claim 14, wherein the price determination processor is configured to calculate the payment amount based at least in part on the zip code of the provider.

16. The computer-implemented method of claim 14, wherein the provider is at least one of the group consisting of: a doctor, a pharmacist, a dentist, an optometrist, and a hospital.

17. The computer-implemented method of claim 14, wherein the price determination processor is further configured to select from amongst a plurality of fee schedules negotiated with one or more provider organizations.

18. The computer-implemented method of claim 14, wherein the payment amount comprises a portion to be paid by the patient and a portion to be paid from a source of medical funds.

19. The computer-implemented method of claim 18, wherein the source of medical funds is a third-party payor.

20. The computer-implemented method of claim 18, wherein the source of medical funds is a Flexible Savings Account.

* * * * *